United States Patent [19]
Gory et al.

[11] Patent Number: 5,649,906
[45] Date of Patent: *Jul. 22, 1997

[54] METHOD FOR IMPLANTING A REMOVABLE MEDICAL APPARATUS IN A HUMAN BODY

[76] Inventors: Pierre Gory, 02, Boulevard Clémenceau; Gilles Bovyn, 03, rue Monseigneur Morelle, both of 22000 Saint-Brieuc, France

[*] Notice: The term of this patent shall not extend beyond the expiration date of Pat. No. 5,300,086.

[21] Appl. No.: 374,835

[22] Filed: Jan. 19, 1995

Related U.S. Application Data

[63] Continuation-in-part of Ser. No. 209,414, Mar. 9, 1994, Pat. No. 5,415,630, which is a continuation of Ser. No. 985,178, Dec. 2, 1992, Pat. No. 5,300,086, which is a continuation-in-part of Ser. No. 731,536, Jul. 17, 1991, abandoned.

[51] Int. Cl.$^6$ .................................................. A61M 31/00
[52] U.S. Cl. ........................... 604/53; 604/175; 606/108; 606/198
[58] Field of Search ........................ 604/49, 52, 53, 604/96, 104–106, 164–165, 171, 175, 280; 606/192, 194, 198, 200, 108

[56] References Cited

U.S. PATENT DOCUMENTS

| | | |
|---|---|---|
| 3,829,903 | 8/1974 | Stati . |
| 3,932,656 | 1/1976 | Ramwell . |
| 4,218,255 | 8/1980 | Bajpai . |
| 5,090,954 | 2/1992 | Geary ........................................ 604/29 |
| 5,383,887 | 1/1995 | Nadal ....................................... 606/200 |

FOREIGN PATENT DOCUMENTS

| | | |
|---|---|---|
| 0533511 | 7/1992 | European Pat. Off. . |

OTHER PUBLICATIONS

Furman (ed), "Advances in Cardiac Pacemakers," *Annals of the NY Academy Sciences*, Oct. 30, 1969, pp. 858–868.

*Primary Examiner*—Corrine M. McDermott
*Attorney, Agent, or Firm*—Morrison Law Firm

[57] ABSTRACT

A method for removably implanting in an implantable zone of a human body, preferably a vein, a divisible and flexible stem is disclosed. The stem includes a distal end and a proximal end, and may further includes a medical apparatus or implant fixed to one end of the stem. The method includes forming an access route to an implantation zone in a human body, followed by introducing a medical apparatus or implant into the body through the access route with the distal end of the stem first so as to implant the apparatus in the implantation zone, the stem having a length sufficient to extend along the route. The method further includes providing a locating member on a proximal end of the stem, the member being adapted to being disposed subcutaneously for locating the stem through the skin of the patients body. Thereafter, the locating member and the proximal end of the stem are disposed subcutaneously in the body in proximity to the access route. The step of disposing includes forming within the patients body in proximity to the access route, a small space for disposing therein the locating member fixed to the proximal end. After temporary implanting an implant, a removable strengthening cable can be inserted in the stem in order to displace the implant along the sheath during its positioning in an implantable zone such as a vein, in particular in the inferior vena cava of a patient. This implant can be easily removed after a certain period, when the risks of pulmonary embolism for example, is no longer feared. In the present invention, the medical apparatus may include at least one of a stent and a drug delivery means.

8 Claims, 4 Drawing Sheets

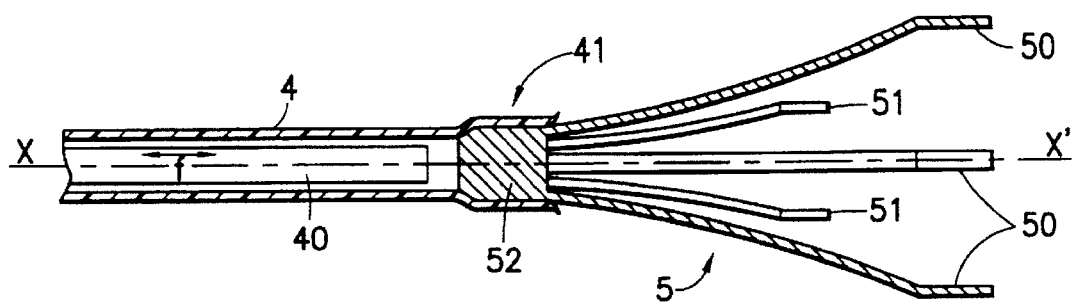
FIG. 2
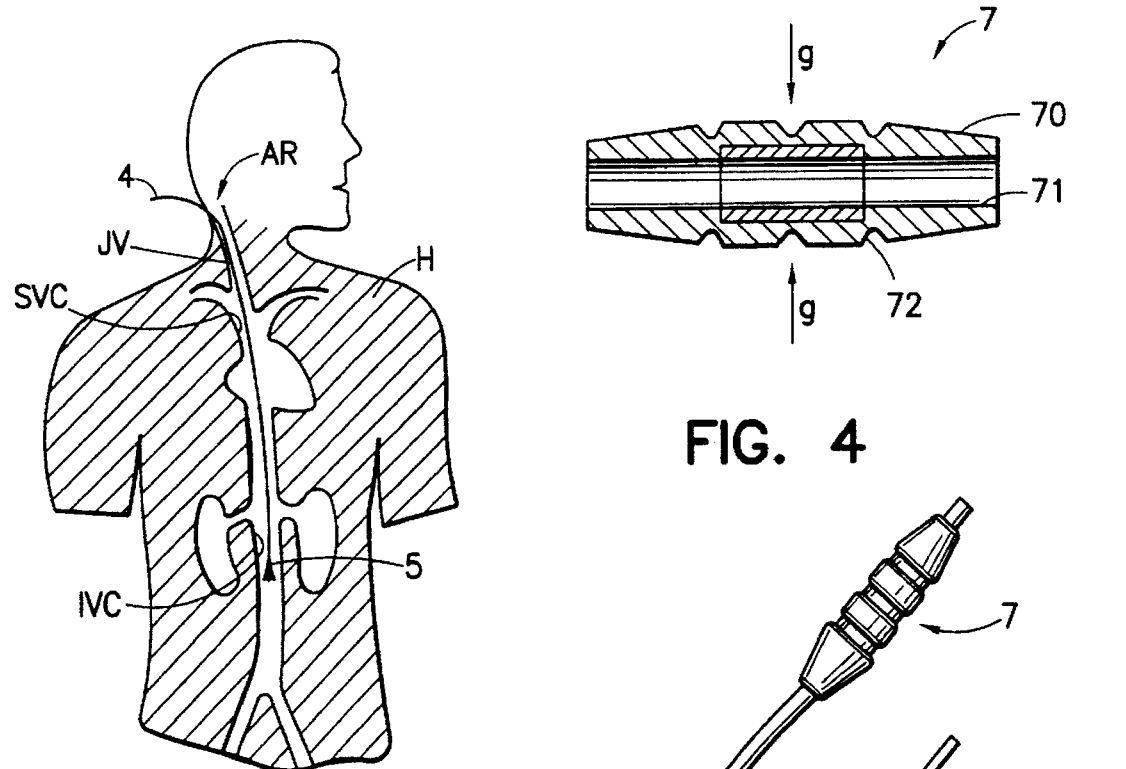
FIG. 3
FIG. 4
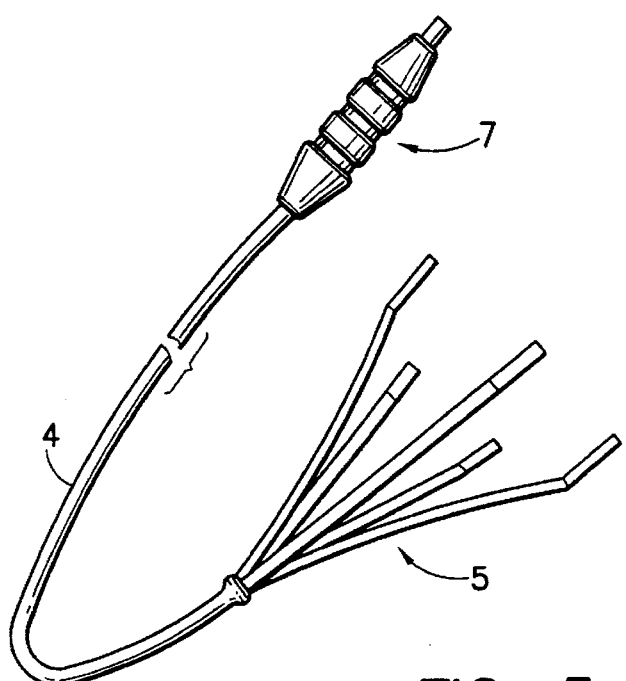
FIG. 5

METHOD FOR IMPLANTING A REMOVABLE MEDICAL APPARATUS IN A HUMAN BODY

This application is a continuation-in-part application of application Ser. No. 08/209,414, filed Mar. 9, 1994, now U.S. Pat. No. 5,415,630 which, in turn, was a continuation application of application Ser. No. 07/985,178, filed Dec. 2, 1992, now U.S. Pat. No. 5,300,086 which, in turn, was a continuation-in-part application of application Ser. No. 07/731,536, filed Jul. 17, 1991, now abandoned.

BACKGROUND OF THE INVENTION

This invention relates to a device for temporarily implanting, in an implantable duct of a human body, and in particular in a vein of a mammal including a human, a divisible and flexible stem which may be further provided with a medical apparatus or implant fixed at one end of the stem, and more particularly a blood filter of the type that is elastically expandable in the radial direction.

If such a medical apparatus includes a blood filter, its function as a blood filter is to hold back the blood clots that may form in the course of phlebitis or other vascular or cardiovascular disorders, in order to prevent their migration towards the pulmonary arteries where they could cause an embolism.

The filters generally used for this purpose have the shape of a small umbrella consisting of a plurality of flexible branches that can be radially expanded. In the rest position (retracted state) the branches extend approximately parallel to one another and occupy a reduced dimension in the radial direction, and this allows them to be positioned in a vein. Once in place inside the vein, the branches spread automatically outward and are immobilized against the wall of the vein, thereby anchoring the filter at the desired site.

Filters of this type are preferably positioned in the inferior vena cava, a little below the level of the kidneys.

The equipment that permits positioning of the filter traditionally comprises a guide rod and a mandrel which make it possible to insert a sheath into the vein to the desired depth, in such a way that the end of the sheath arrives at the site where the filter is to be positioned. When the filter is positioned in the inferior vena cava, it is known to carry out the implanting via a percutaneous access route or by "denudation" at the level of the fight internal jugular vein.

The positioning is thus carried out starting from the jugular vein, and via the superior vena cava. After the sheath is positioned, the mandrel and the guide rod are withdrawn. The filter is then introduced into the sheath by a special syringe and displaced inside the sheath, along its entire length, by the mandrel, the latter in this case having the role of a pusher. When the filter arrives at the free end of the sheath (previously positioned at the desired site in the inferior vena cava), the filter spreads open automatically and anchors in the wall of the vein. The sheath is then removed, and the filter remains permanently in position.

The main disadvantage of this technique is that the filter can be withdrawn only by performing a very delicate surgical operation. Unfortunately, the permanent positioning of the filter in the vena cava is a source of complications, in particular, the filter can trigger a thrombosis. Moreover, the patient must take anticoagulant medication for for as long as the filter is in place.

These disadvantages are all the more regrettable since, in a great many forms of treatment, the positioning of the filter in the vein is necessary only for a limited period, generally a few weeks or a few months, corresponding to the period during which there is a real risk of embolism.

For this reason a technique has recently been proposed for implanting the filter temporarily and removably, so it can be withdrawn after a certain time has elapsed.

For this, the mandrel which is used for implanting the filter is permanently integral with the latter; after the filter is implanted, the mandrel remains inserted in the vein and projects from the body via the access route used for the implanting, that is, at the level of the neck, in the region of the jugular vein, when the filter is implanted in the vena cava. Unfortunately, such a rod, which is relatively rigid, is very uncomfortable for the patient; moreover, because the mandrel projects from the skin, it constitutes a source of infection that may lead to serious complications, especially septicaemia.

Similar problems occur when, for example, certain types of stents or medical probes are to be used.

The function of a stent is to hold open a vessel for maintaining a palency of said vessel.

European Patent #EP-533,511 discloses a "Device for maintaining substantially the patency of a bodily duct section of a patient, therefrom said device is removable, comprising an outer axially elongated catheter within which a radially self-expendable mesh can be retracted, said outer catheter having a distal portion slidable in said duct section and a proximal portion extendable externally from said patient body, an internal axially elongated operating member having a distal portion to which is connected said mesh which comprises a plurality of interwoven resilient wires, said operating member being slidable within said outer catheter for connecting said mesh to outside said body and controlling therefrom the movements of the mesh." The function of the operating stem is to remotely control the position of the expandable stent member when it is implanted in the vessel.

Because such an operating stem projects from the skin when the stent apparatus is implanted, risks of infection exist. And the projecting stem is very uncomfortable for the patient.

Identical problems occur with all medical apparatus implantable in a duct of the body of a patient (human or animal), if said apparatus comprises a stem or a catheter which is implanted in the body.

In other words, it is to be understood that any flexible stem can be a source of infection and uncomfortable for the patient if said stem projects from the patient's skin.

OBJECTS AND SUMMARY OF THE INVENTION

An object of the present invention is to overcome the disadvantages of the prior art with a new device for implanting in a bodily duct of a patient, a medical apparatus comprising a divisible stem filter of the type mentioned above, this device being simple to manipulate, use, and implant reversibly, without the patient being exposed to real risks of infection or being traumatized by the presence of the implanted device throughout the period during which the medical apparatus must remain in place.

In the description and claims that follow, the terms "proximal" and "distal" are used with reference to the point on the body of the patient through which the medical implant is introduced up to its implantation zone. According to this definition, the proximal end of an element is that which is nearest the point of introduction, and the distal end is that which is furthest away from that point.

The device of the present invention is provided with a locating member adapted to be disposed subcutaneously for localizing, through the skin of the patient, the stem to whose distal end a medical intervention means may be fixed. Especially to avoid infection, if the stem is a catheter, the locating member will comprise a sleeve of a bio-compatible material that encloses an internal closing means at the catheter's proximal end. The internal closing means can close off the catheter.

Further, especially if the medical intervention means is a blood filter to be implanted in a blood vessel, the apparatus of the present invention will advantageously be composed of the following elements:

a) an elastic guide wire of small diameter intended to be inserted into the vein via a percutaneous access route or after denudation;

b) a semi-rigid tubular mandrel capable of being fitted onto the guide wire and displaced along the guide wire;

c) a thin-walled tubular sheath capable of being fitted onto the mandrel and positioned inside the vein by displacing the mandrel along the guide wire;

d) the catheter having the form of an easily divisible flexible tube whose distal end permanently holds the blood filter;

e) a strengthening cable capable of being inserted in a removable manner into the catheter, thereby making it possible to displace, inside the previously positioned sheath, the catheter and its filter in the retracted state, until the latter emerges at the distal end of the sheath and spreads open automatically to anchor against the wall of the vein;

f) the locating member, which is thus intended to be fixed at the proximal end of the catheter after removing the strengthening cable and cutting the catheter at the level of the access route.

Furthermore, according to a certain number of advantageous but not restrictive characteristics:

the proximal ends of the mandrel and of the sheath each bear a head in the form of a female sleeve that meets LUER international standards. The head borne by the mandrel is adapted to butt against the head borne by the sheath, in order to facilitate their point positioning inside the vessel;

the device comprises a tubular syringe body, fitted onto the catheter, that receives the blood filter and holds the latter in the retracted state;

the proximal end of the head borne by the sheath and the distal end of the syringe body are provided with complementary coupling means that satisfy the so-called "LUER-Lock" standards, such as a threading/tapping, thereby facilitating the introduction of the filter into the previously positioned sheath;

the locating member has the form of a sleeve intended to be crimped onto the catheter;

the locating member is a sleeve free from sharp angles, for example, it may be ovoid in shape;

the locating member is made of plastic material cast on a metal ring;

if the metal deformable ring is closely crimped onto the catheter, it can constitute the above-mentioned catheter proximal-end closing means. Otherwise, a plug inserted into the catheter end through the central opening of the sleeve can be used as such a closing means;

the catheter is made of plastic material, for example, polyvinyl chloride covered with a bio-compatible material such as a silicone-based material;

the distal end of the mandrel bears a radiopaque marker, for example, a metal ring;

the distal end of the catheter, which bears the medical intervention means, is also closed. In many cases this feature could be important, since it prevents blood flowing back into the catheter towards the catheter's proximal end. Further, if the catheter is thus closed at both its distal and its proximal ends, the risk of infection will be further limited.

Briefly stated, there is provided a method for removably implanting in an implantable zone of a human body, preferably a vein of a human being, a divisible and flexible stem. The stem include a distal end and a proximal end, and may further includes a medical apparatus or implant fixed to one end of the stem.

The method includes forming an access route to an implantation zone in a human body, followed by introducing a medical apparatus or implant into the body through the access route with the distal end of the stem first so as to implant the apparatus in the implantation zone, the stem having a length sufficient to extend along the route.

The method further includes providing a locating member on a proximal end of the stem, the member being adapted to being disposed subcutaneously for locating the stem through the skin of the patients body. Thereafter, the locating member and the proximal end of the stem are disposed subcutaneously in the body in proximity to the access route. The step of disposing includes forming within the patients body in proximity to the access route, a small space for disposing therein the locating member fixed to the proximal end.

After temporarily implanting an implant, a removable strengthening cable can be inserted in the stem in order to displace the implant along the sheath during its positioning in an implantable zone such as a vein, in particular in the inferior vena cava of a patient. This implant can be easily removed after a certain period, when the risks of pulmonary embolism are no longer feared. In the present invention the medical apparatus may include at least one of a filter, a stent, a balloon, or a drug delivery means.

According to an embodiment of the present invention, there is provided a method for medically operating within a patient's body by means of an implantable apparatus including a divisible stem implantable within the body, the stem having a proximal and a distal end.

The method includes the steps of forming an access route to an implantation zone in the body, introducing the apparatus into the body through the access route with the distal end of the stem first so as to implant the apparatus in the implantation zone, the stem having a length sufficient to extend along the route.

This is followed by providing a locating member on the proximal end of the stem, the locating member being adapted to being disposed subcutaneously for locating the stem through the skin surface of the body, disposing the locating member and the proximal end of the stem subcutaneously in the body in proximity to the access route wherein the step of disposing includes forming, within the patient's body in proximity to the access route, a small space for disposing therein the locating member fixed to the proximal end, and closing the small space in which is disposed the locating member fixed to the proximal end of the stem, whereby the locating member and the stem remain disposed in the body.

According to another embodiment of the present invention, a method is provided for medically operating within a patient's body by means of an implantable apparatus including a divisible extension stem implantable within the body, the stem having a proximal and a distal end. The method includes the steps of forming an access route to an implantation zone through a skin surface of the body, and introducing the apparatus into the body through the access route with the distal end first so as to implant the apparatus in the implantation zone, the stem having a length sufficient to extend along the route.

Wherein the length of the stem is such that the proximal end thereof extends out of the patient's body when the apparatus is introduced into the blood vessel, the method includes the further step of cutting the stem at the proximal end before providing the proximal end with the locating member, whereby the length of the stem is adapted to the length of the access route.

The method includes providing a locating member on the proximal end of the stem, the locating member being adapted to being disposed subcutaneously for locating the stem through the skin surface of the body.

The method includes disposing the locating member and the proximal end of the stem subcutaneously in the body in proximity to the access route, and closing the access route, whereby the locating member, the stem, and the apparatus remain subcutaneously disposed in the body.

According to yet another embodiment of the present invention, there is provided a method for medically operating within a patient's body by means of an implantable apparatus including a medical intervention means medically operating within an implantation zone of the body and a divisible extension stem implantable within the body, the stem having a proximal and a distal end, and the medical intervention means being fixed to the distal end.

The method includes the steps of forming an access route to an implantation zone through a skin surface of the body, introducing the apparatus into the body through the access route with the medical intervention means first so as to implant the intervention means in the implantation zone, the stem having a length sufficient to extend along the route, and providing a locating member on the proximal end of the stem, the locating member being adapted to being disposed subcutaneously for locating the stem through the skin surface of the body.

The method includes disposing the locating member and the proximal end of the stem subcutaneously in the body in proximity to the access route. The step of disposing includes forming, within the patient's body in proximity to the access route, a small space for disposing therein the locating member fixed to the proximal end, and closing the access route, whereby the locating member, the stem, and the medical intervention means remain disposed in the body.

According to a further embodiment of the present invention, a method is provided wherein the stem is a catheter, and wherein the step of introducing the apparatus further includes introducing through the access route, a guide wire, the guide wire extending to the implantation zone in which the medical intervention means is to be implanted, introducing around the guide wire an elongated mandrel disposed within an elongated sheath, withdrawing the guide wire and the mandrel from the patient's body, providing the catheter with an inner strengthening cable adapted to be removably disposed within the catheter, introducing, into the sheath extending to the implantation zone, the medical intervention means first and then the catheter, withdrawing the sheath from the patient's body while leaving the medical intervention means in the implantation zone, withdrawing the strengthening cable from the catheter, and cutting the catheter at the proximal end, near the skin surface.

An alternative embodiment contemplates an apparatus to be removably implanted in a mammalian body, including a human body, for medically operating within an implantable zone of the body, the apparatus including a divisible stem adapted for implanting in the body, the stem having a proximal and a distal end, and a locating member adapted to be disposed subcutaneously for locating the stem through a skin surface of the mammalian body after the stem is implanted.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 2 shows in longitudinal cross-section the distal end of the catheter fitted with the blood filter.

FIG. 3 is a diagrammatic view illustrating the positioning of the filter in the inferior vena cava of a patient.

FIG. 4 is a longitudinal cross-sectional view of a first embodiment of the locating member.

FIG. 5 is a diagrammatic view of the catheter whose proximal end is provided, with the embodiment of the locating member shown in FIG. 4 and whose distal end is provided with the blood filter of FIG. 2.

DETAILED DESCRIPTION OF THE PREFERRED EMBODIMENTS

Figure 1:
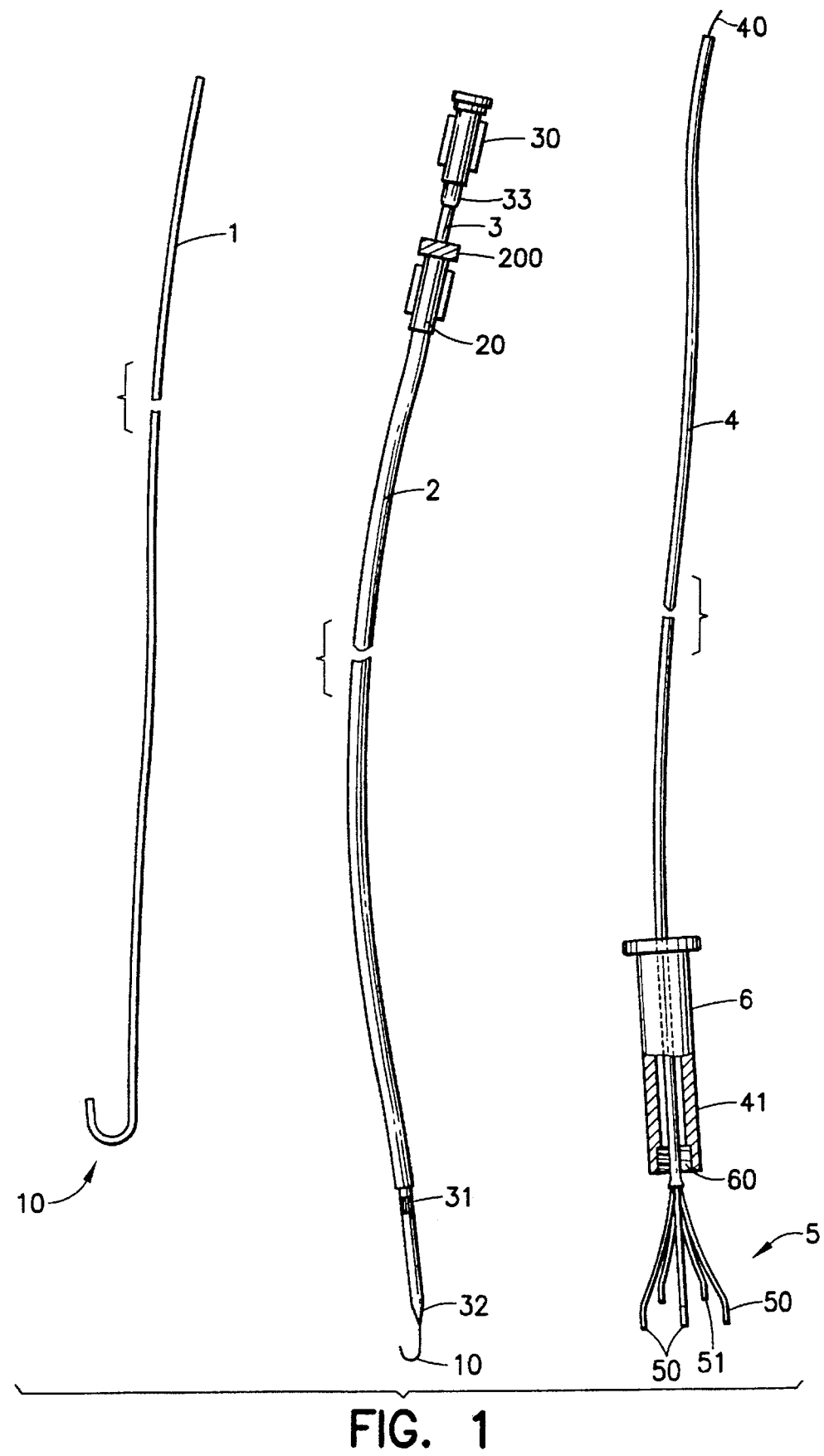
FIG. 1 shows the various elements constituting the device, especially if the medical apparatus to be implanted is a blood filter.

The various main elements constituting the device and shown in the drawings have been given reference numbers as follows: a guide wire 1, a tubular sheath 2, a tubular mandrel 3, a catheter 4, a filter 5, a strengthening cable 40, a locating member 7, and a syringe body 6.

Referring to FIG. 1, guide wire 1 is a wire of small diameter, made, for example, of metal, which, though elastically flexible, possesses a certain rigidity. Guide wire 1 has a distal end 10 that is curved to form a half loop, which gives guide wire 1 the general appearance of the letter J.

Sheath 2 is a thin-walled, cylindrical tube made of plastic material, for example, polyvinyl chloride. It is open at its two ends. At its proximal end, it holds a sleeve-shaped sheath head 20, likewise of plastic material, whose diameter is greater than the external diameter of tubular sheath 2. Tubular sheath 2 has a certain flexibility. On the free end (proximal side) of sheath head 20 is a threading 200 consisting of one or more threads (LUER-Lock standards).

Tubular mandrel 3 consists of a rod made of semi-rigid plastic material whose internal diameter corresponds to the diameter of guide wire 1, thereby allowing tubular mandrel 3 to be fitted onto guide wire 1. Mandrel 3's external diameter corresponds to the internal diameter of tubular sheath 2, thereby allowing tubular sheath 2 to be fitted onto tubular mandrel 3.

The fitting of tubular mandrel 3 onto guide wire 1 and of tubular sheath 2 onto tubular mandrel 3 leaves sufficient play to permit relative longitudinal sliding of these three elements.

Tubular mandrel 3 holds at its proximal end a sleeve-shaped head 30 of LUER standards. Sleeve-shaped 30 has a cylindrical or slightly conical extension 33 which is adapted to be engaged in a complementary seat provided in sheath head 20. After engagement of their respective heads, tubular sheath 2 and tubular mandrel 3 are perfectly integral with one another to such an extent that, by manipulating only one of the two heads 20, 30, it is possible to displace the entire assembly of tubular mandrel 3 and tubular sheath 2. Tubular mandrel 3 has a distal end 32 of a smooth, conical shape with a rounded tip, thereby avoiding trauma during implanting of the device.

At a short distance from distal end 32, tubular mandrel 3 is provided with a radiopaque marker 31, consisting, for example, of a small metal ring. The relative lengths of tubular sheath 2 and of tubular mandrel 3 are determined so that, after complete insertion of tubular mandrel 3 into the tubular sheath 2 (with head 30 in abutment against head 20), radiopague marker 31 just emerges at the distal end of tubular sheath 2.

Catheter 4 consists of a very flexible (nonrigid) tube whose external diameter is substantially smaller than that of tubular sheath 2. Catheter 4 is made of a plastic material covered with a bio-compatible material such as a silicone-based material; the plastic material is, for example, polyvinyl chloride. Tubular mandrel 3 is advantageously made radiopaque, for example by including particles of barium sulfate in the material of which it is made.

As already mentioned, catheter 4 has a tubular shape, and it can receive in its central lumen strengthening cable 40 of corresponding diameter, this cable consisting, for example, of a very thin wire of spring steel wound spirally about itself over its entire length.

As will be seen more particularly in FIG. 2, the distal end of catheter 4 is closed by a closure plug 52 which forms part of filter 5. The sliding of strengthening cable 40 in catheter 4 (sliding indicated by the double arrow f in FIG. 2) is thus limited in the distal direction, so that the cable serves as a pusher upon introduction of the catheter, as will be explained hereinbelow.

Filter 5 is a filter of a type known per se, of the kind described in the background section of the present description. In the embodiment illustrated, filter 5 has the form of an umbrella frame which comprises eight branches consisting of thin flexible metal strips. There are four long branches 50 alternating with four shorter branches 51 in a uniform angular distribution of 45°.

These branches 50, 51 are embedded at their proximal ends in the closure plug 52 of catheter 4. Their distal ends are slightly curved to present a direction essentially parallel to the longitudinal axis X—X both of filter 5 and of catheter 4. When the filter is in the unfurled state (state illustrated in the figures), the free ends of branches 50 and 51 come to lie correctly against the wall of the vein without risk of trauma to the vein.

The device also comprises syringe body 6 of plastic material, which has the shape of a tubular sleeve. Syringe body 6 is able to slide on catheter 4. The length of syringe body 6 is slightly greater than the length of branches 50 of filter 5. Its internal diameter corresponds essentially to the internal diameter of sheath head 20 and of tubular sheath 2.

The distal end of syringe body 6 is tapped in such a way as to present a thread 60 complementary with a threading 200 of sheath head 20 in accordance with LUER standards.

Locating member 7, illustrated in FIGS. 4 and 5, comprises a body 70 in the shape of a small sleeve made of flexible plastic material. This sleeve, free of sharp angles, has the general shape of a small olive whose more bulging central part is cast on a metal ring 72.

As is illustrated in FIG. 4 by arrows g, crimping of the locating member 7 onto a rod previously fitted into a central hole 71 of body 70, and consequently fixing of member 7 on this rod, can be easily obtained by crushing the central zone of the sleeve and deformation of ring 72. As seen in FIG. 5, it is thus possible to fix locating member 7 at the proximal end of catheter 4 in a simple manner.

We will now explain how the device which has just been described is used for positioning a blood filter in the inferior vena cava of a human body, and this in a reversible manner, it being possible for the filter to be easily removed later.

The filter is implanted under local anesthesia, which is designated H in FIG. 3. In the conventional manner, the surgeon begins by forming in the neck a percutaneous access route AR in the right internal jugular vein JV, or by carrying out denudation.

In a first stage, he introduces guide wire 1 into the jugular vein. With radiological monitoring, made possible by the radiopacity of the wire, he lowers guide wire 1 through the jugular vein and then makes it follow the superior vena cava SVC and then the inferior vena cava IVC. Because distal end 10 of guide wire 1 is curved, distal end 10 does not cause hitching or trauma during its displacement. This operation finishes when distal end 10 has arrived slightly beyond the zone where the filter is to be implanted, below the bifurcations of renal irrigation.

He then makes a small incision for widening on both sides of the entry point of the guide, in order to facilitate the operation which follows.

In a second stage, with sleeve-shaped head 30 sheath being in abutment against head 20, the surgeon fits onto the proximal end of guide wire 1 (which of course protects from the jugular vein) the single assembly consisting of tubular mandrel 3 and tubular sheath 2; he lowers this assembly gently along guide wire 1 until radiopaque marker 31 reaches the zone intended for anchoring filter 5.

In a third stage, he withdraws guide wire 1 and tubular mandrel 3 from tubular sheath 2.

In a fourth stage, while syringe body 6 covers filter 5, which is consequently in its folded state, he connects syringe body 6 onto sheath head 20 by complementary screwing means 60, 200.

In a fifth stage, with strengthening cable 40 situated inside catheter 4, he lowers this assembly so that filter 5, still in the retracted state, is transferred first into sheath head 20 and then into tubular sheath 2. The pushing force applied by the surgeon on the distal end of the catheter 4/strengthening cable 40 assembly is transmitted correctly to the filter on account of the strengthening role of the cable, so that the filter descends progressively along tubular sheath 2. This would be difficult in the absence of strengthening cable 40 on account of the flexibility of the catheter (which is semi-rigid).

When the filter has arrived at the distal end of tubular sheath 2, it spreads open automatically as a result of the flexibility of branches 50, 51, which come to bear against the walls of the vena cava at the desired site, and this accomplishes the anchoring of filter 5.

In a sixth stage, the surgeon withdraws tubular sheath 2 from the vein.

In a seventh stage, he withdraws strengthening cable 40 from catheter 4 and then cuts catheter 4 outside the jugular vein, at a short distance from the jugular vein. This cutting can be carded out conveniently on account of the easily divisible nature of the catheter, for example, using a pair of ordinary surgical scissors.

In an eighth stage, the surgeon fits onto the protruding proximal end of the catheter locating member 7, then fixes it by crimping with the aid of a suitable tool, for example, a pincer.

Finally, the surgeon forms, via the small widening incision, a small space under the platysma of the neck, where he tucks in locating member 7. He then closes percutaneous access route AR in a conventional manner, in such a way that locating member 7 remains confined under the skin after suturing. There is therefore no risk of infection by the transcutaneous route at the level of the neck.

It should also be noted that the fact that the catheter 4 is closed at its distal end prevents any risk of blood flowing back into the catheter in the direction of percutaneous access route. In addition, the crushing of locating member 7 on catheter 4 also causes the sealing of catheter 4 at its proximal end.

On account of its flexibility, the catheter does not in any way inconvenience the patient and does not interfere with his activities; it is completely "forgotten" by the patient throughout the period during which the filter must be kept in position in the inferior vena cava. The duration of retention of the catheter and of the filter can range from a few weeks to several months by virtue of the invention, whereas it is only two to three weeks in the techniques of temporary positioning used hitherto, with the risks of infection associated with these techniques.

It is possible at any given time to check the position of locating member 7, either by palpating the skin of the patient or by X-ray. When the filter is to be removed, it suffices to reopen percutaneous access route AR and to remove filter 5 from the vein by pulling on the end of the catheter 4. The special shape of the filter 5, which can contract freely inward, permits its displacement along the veins IVC, SVC and JV.

The possible principal dimensions of the device are given hereinbelow purely by way of indication.

Tubular mandrel 3 and tubular sheath 2 can have a length of the order of 50 to 65 cm; catheter 4, a length of the order of 60 to 80 cm; guide wire 1 and strengthening cable 40, lengths of the order of 80 to 100 cm.

Guide wire 1 and strengthening cable 40 can have a diameter of the order of 0.5 to 0.7 mm; tubular mandrel 3 and tubular sheath 2 can have external diameters of the order of 3.5 and 4.2 mm, respectively, while catheter 4 can have an external diameter of the order of 2 mm. Long branches 50 of filter 5 can have a length of the order of 40 mm, while its short branches 51 can have a length of the order of 25 mm.

After the device is positioned, the effective length of the catheter, that is, the length between filter 5 and locating member 7, will generally be between 40 and 55 cm.

All the elements constituting the device which is the subject of the invention are intended to be packaged in one and the same sterile packaging, for single use, with a view to their sale and their delivery to medical/surgical treatment centers.

It should be clear that other embodiments of a locating member than those illustrated in FIGS. 4 and 5 could be used in the present invention.

Figure 6:
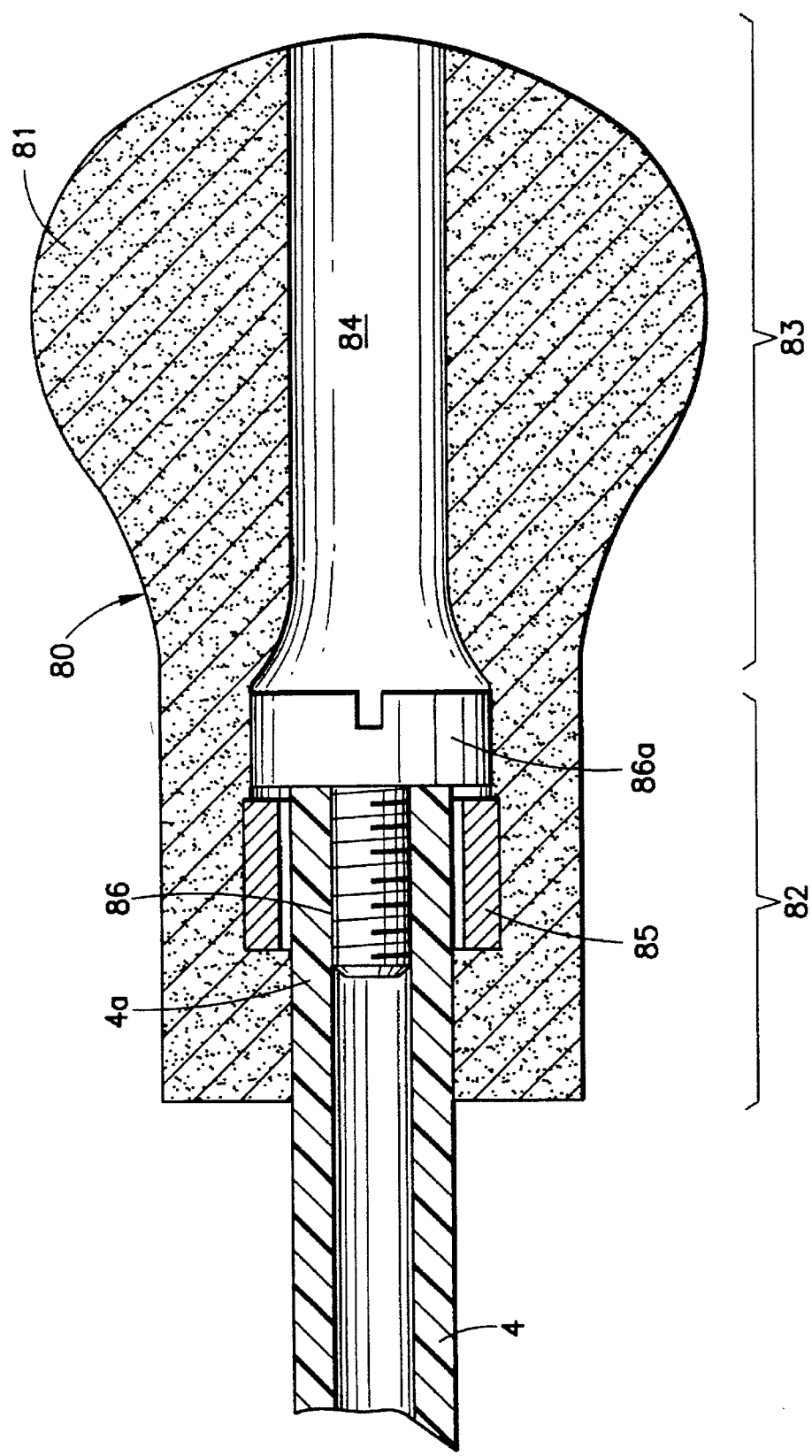
FIG. 6 is a longitudinal cross-sectional view of the proximal end of the catheter to which is fixed a second embodiment of the locating member.

Referring to FIG. 6, one alternative embodiment has a locating member 80 that comprises a sleeve 81 made of a soft plastic material (such as silicone) and having a generally rounded external shape with a cylindrical front portion 82 that has a circular cross-section. Front portion 82 is linked to a substantially spherical or ovoid rear portion 83.

The two portions of sleeve 81 are coaxially crossed through by a central aperture 84 wherein is engaged a proximal end 4a of catheter 4. Proximal end 4a is engaged in aperture 84 within front portion 82 to penetrate through a ring 85 enclosed in sleeve 81 coaxially with aperture 84. Ring 85 is deformable, and can be made of metal, so that it can be crimped or clamped with sleeve 81 on proximal end 4a. In this embodiment, proximal end 4a is closed by a plug 86 engaged therein. Plug 86 can consist of a screw (or its equivalent, such as a notched plug) having an enlarged head 86a extending into aperture 84 and operable therethrough by an appropriate screwdriver. Of course, locating member 80 will be disposed around catheter 4 after division thereof, as previously described.

Figure 7:
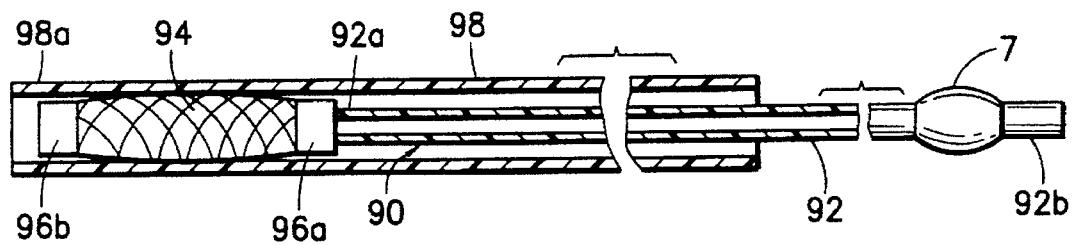
FIG. 7 shows a stem whose proximal and distal ends are provided, respectively, with the locating member shown is FIG. 4 and with a stent, in a contracted state.

For example in FIG. 7 it is shown a removable stent apparatus 90 as illustrated in EP-A-05335 11. Stent apparatus 90 comprises a flexible and divisible catheter 92 fixed at its distal end 92a to a self-radially expandable tube-shaped metallic wire netting or mesh 94. Mesh 94 forms a basket the two tube ends of mesh 94 are connected (e.g. welded or crimped) to proximal and distal bushings 96a, 96b. Proximal bushing 96a is further connected around catheter 92, while distal bushing 96b is free to move. The wire mesh 94 consists of several elastic and elongated wire members possibly in the form of "struts" which are interwoven with each other. These wire members can be spiral-shaped spring steel wires. At proximal end 92b, catheter 92 is surrounded by the locating member 7 which is crimped therearound.

Figure 8:
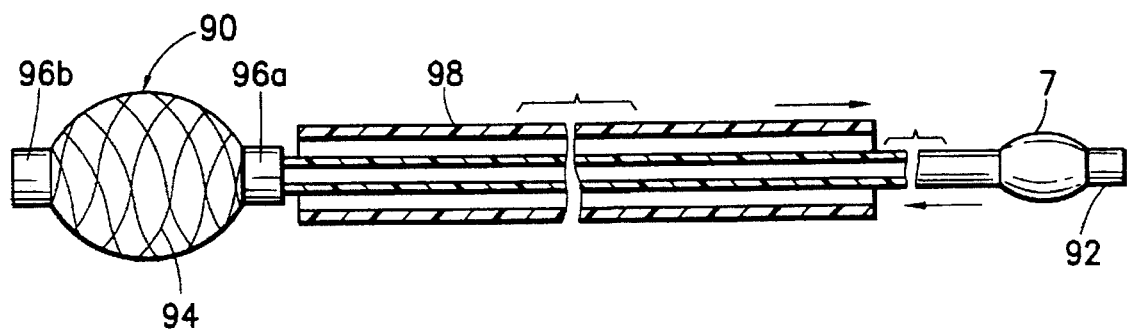
FIG. 8 shows the apparatus of FIG. 7 in a state in which the stent is radially expanded.

For implanting such a stent apparatus, a percutaneous access route can be used (method of Seldinger). A thin metallic axial guiding wire is first introduced into the vessel. Then, a sheath 98 similar to tubular sheath 2 is fitted onto said guiding wire, together with its tubular mandrel 2. Tubular mandrel 3 is withdrawn from sheath 98. Stent apparatus 90, previously radially contracted, is introduced into tubular sheath 2. In FIG. 8, the sheath is referenced 98. When mesh 94 arrives at a distal end 98a of sheath 98, it automatically radially expands as a result of the flexibility of the mesh wire (see FIG. 8) then comes to bear against the wall of the corresponding vessel. In the following step the sheath is withdrawn from the body and stem 92 is equipped with the locating member 7, as previously explained in relation to the blood filter 5.

Figure 9:
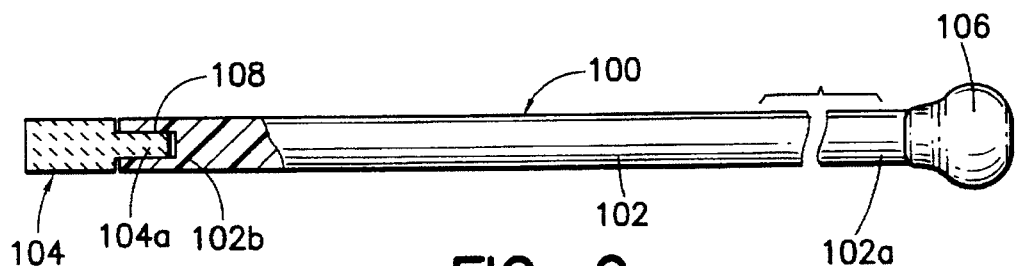
FIG. 9 shows a stem whose proximal end is provided with a locating member and whose distal end is cut away to show a provided drug dispensing means.

In FIG. 9, another medical apparatus is illustrated. It is a medical drug dispensing implant 100 comprising an elongated flexible and divisible stem 102 and a drug dispensing means 104. Further, stem 102 is provided with a locating member 106 at its proximal end 102a.

Drug dispensing means 104 can be a block of cellulose, ceramic, metal, or certain plastic used as carrier material in which the drug is first absorbed and then released in the body. If powdered drug is compressed together with powdered plastic, a porous tablet or block will form in which the plastic material will partly cover the surface of the powdered drug and will delay its release. In U.S. Pat. No. 4,218,255 which is incorporated in the present description by reference, the carrier is a porous ceramic crystalline structure of interconnecting pores capable of the critical controlled time release of pharmaceutical preparations such as proteins, polypeptides, hormones, and other small molecular weight active materials. The ceramic is comprised of aluminum oxide ($Al_2O_3$), calcium oxide (CaO) and phosphorus pentoxide ($P_2O_5$) in a controlled weight percent mixture of about 50%, 38% and 12%, respectively. In the process of making, the mixture is calcined and then again grounded, sieved and mixed with a binder. The mixture is compressed and sintered at a predetermined temperature. The resulting compound in which is dispersed Coy injection or immersion) the drug can have the form of a block (see FIG. 9). Alternatively, the compound can also have a tubular form, for example, having the drug (insulin) in the cavity therein (see column 5 of U.S. Pat. No. 4,218,255).

A further example is to be found in U.S. Pat. No. 3,829,903 which is also incorporated in the present description by reference. U.S. Pat. No. 3,829,903 discloses a medical device for prolonged contact with blood. The medical device is made of silicone rubber having powdered tungsten incorporated therein to inhibit blood clot formation on the device's surfaces. The amount of tungsten metal in powder form in the silicone elastomer is about 0.5 percent by weight. The silicone rubber can be any conventional elastomer stock based on a polydiorganosiloxane gum which contains methyl radicals and additionally organic radicals selected from the group consisting of vinyl radicals and 3,3,3-trifluoropropyl radicals bonded to the silicone atoms of the polydiorganosiloxane gum. The powdered tungsten is thoroughly mixed with the other ingredients before forming the ultimate shape of the article.

Other examples of drug delivering means to be used especially on indwelling medical devices can be found in U.S. Pat. No. 3,932,656 (article of manufacture for instant release of anti-aggregation and non-thrombogenic agents to biological media), or in "Advances in Cardiac Pacemakers," pp. 857–868 (Folkman) published in "Annals New York Academy of Science," Vol 167, Art. 2, Oct. 30, 1969. A silicone rubber compound ("Silastic, reg. trademark") having the form of a cylinder containing a core of solid "silastic cement" through which has been dispersed 20,000 microgram of triiodothyronine is disclosed.

In FIG. 9, drug dispensing means 104 comprising a ceramic of silicone rubber matrix in which is dispersed a "drug" (protein, powdered tungsten, etc.) is fixed to a distal end 102b of stem 102 (which could be a catheter). The matrix 104 adheres to the stem and a part thereof, 104a, is engaged within a terminal recess 108 of stem 102 to be blocked therein. The stem can be made of polyurethane, silicone or equivalent biomedical plastic material used for an implantation in a bodily duct. For fixing the matrix to the stem a plastic or metal ring could be tightly placed around the end of the stem (not illustrated).

The implantation of medical drug dispensing implant 100 can be identical as disclosed above in relation to the stent apparatus, if implant 100 is implanted in a blood vessel. If implant 100 is to be introduced in a natural bodily duct, it can be simply slid into said duct after anesthesia. At the end of the implantation, the proximal end of stem 102 which possibly protrudes from the skin is provided with locating member 106. If the length of the stem 102 is too important, either its proximal end 102a is first cut(to be adapted to the length of the "access route" to the implantation area) and then locating member 106 (which corresponds to member 80 of FIG. 6) is fixed to that cut end. Alternatively, locating member 106 corresponding to locating member 7 of FIG. 4 is crimped at a determined distance from proximal end 102a, then the length "in excess" of the stem is cut. In a further step, the shortened proximal end 102a of stem 102 provided with locating member 106 is disposed subcutaneously in the body, in proximity to said access route (in a small space formed just under the skin) and the access route is closed, whereby the locating member, the stem and the drug dispensing means, remain subcutaneously disposed in the body, until the end of the treatment.

Figure 10:
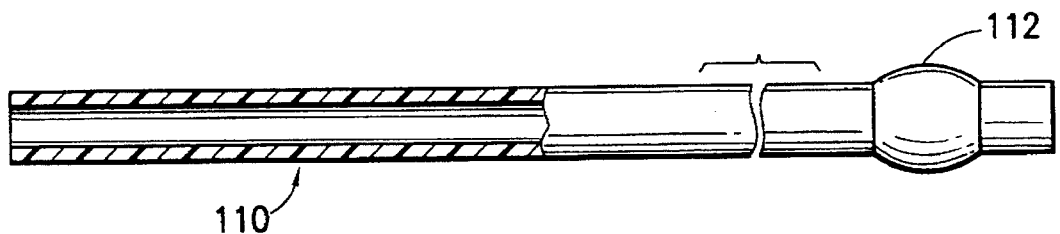
FIG. 10 shows a partially cut away catheter only provided with a locating member at an end.

In FIG. 10, the medical apparatus is only a disposable and flexible catheter 110 whose proximal end is provided with a locating member 112. Locating member 112 can be the one illustrated in FIG. 4 (referenced 7). Such catheter can be implanted in a bodily duct of a patient, for example to be used as a probe or as an indwelling catheter for a long term medical treatment, in situ.

It is to be further understood that the invention generally refers to all medical apparatus or implants comprising a divisible extension stem having a proximal end provided with a locating member adapted to be disposed subcutaneously with the stem for locating said stem (and in general the medical implant) through the skin surface of the body in which the implant has been introduced for a medical intervention in said body.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method for medically operating within a patient's body by means of an implantable apparatus comprising a divisible stem implantable within the body, the stem having a proximal and a distal end, the method comprising the steps of:

forming an access route to an implantation zone in the body;

introducing the apparatus into the body through the access route with the distal end of the stem first so as to implant the apparatus in the implantation zone, the stem having a length sufficient to extend along the route;

providing a locating member on the proximal end of the stem, the locating member being adapted to being disposed subcutaneously for locating the stem through the skin surface of the body;

disposing the locating member and the proximal end of the stem subcutaneously in the body in proximity to the access route;

the step of disposing includes forming, within the patient's body in proximity to the access route, a small space for disposing therein the locating member fixed to the proximal end;

closing the small space in which is disposed the locating member fixed to the proximal end of the stem, whereby the locating member and the stem remain disposed in the body.

2. A method according to claim 1, wherein the stem is a catheter, and wherein the step of introducing the apparatus further comprises:

introducing through the access route, a guide wire, the guide wire extending to the implantation zone in which the apparatus is to be implanted;

introducing around the guide wire an elongated mandrel disposed within an elongated sheath;

withdrawing the guide wire and the mandrel from the patient's body;

providing the catheter with an inner strengthening cable adapted to be removably disposed within the catheter; introducing, into the sheath extending to the implantation zone, the distal end first and then the proximal end;

withdrawing the sheath from the patient's body while leaving the apparatus in the implantation zone;

withdrawing the strengthening cable from the catheter; and cutting the catheter at the proximal end, near the skin surface.

3. A method according to claim 1, wherein:

said implantation zone is a blood vessel; and said step of forming an access route includes one of forming said access route percutaneously and forming said access route by denudation of said blood vessel.

4. A method for medically operating within a patient's body by means of an implantable apparatus comprising a divisible extension stem implantable within the body, the stem having a proximal and a distal end, the method comprising the steps of:

forming an access route to an implantation zone through a skin surface of the body;

introducing the apparatus into the body through the access route with the distal end first so as to implant the apparatus in the implantation zone, the stem having a length sufficient to extend along the route;

wherein the length of the stem is such that the proximal end thereof extends out of the patient's body when the apparatus is introduced into the body;

cutting the stem at the proximal end before providing the proximal end with a locating member, whereby a remaining length of the stem is adapted to the length of the access route;

providing the locating member on the proximal end of the stem, the locating member being adapted to being disposed subcutaneously for locating the stem through the skin surface of the body;

disposing the locating member and the proximal end of the stem subcutaneously in the body in a position in proximity to the access route; and closing the access route, whereby the locating member, the stem, and the apparatus remain subcutaneously disposed in the body with the position of the locating member being discoverable by palpation.

5. A method according to claim 4, wherein:

the divisible stem is a catheter;

the implantation zone is in a blood vessel;

a vascular intervention means is fixed to the distal end of the stem; and the step of introducing the apparatus into the body comprises the step of introducing the vascular intervention means into the blood vessel.

6. A method for medically operating within a patient's body by means of an implantable apparatus comprising a medical intervention means adapted for medically operating within an implantation zone of the body and a divisible extension stem implantable within the body, the stem having a proximal and a distal end, and the medical intervention means being fixed to the distal end, the method comprising the steps of:

forming an access route to an implantation zone through a skin surface of the body;

introducing the apparatus into the body through the access route with the medical intervention means first so as to implant said intervention means in the implantation zone, the stem having a length sufficient to extend along the route, said step of introducing including: introducing through the access route, a guide wire, the guide wire extending to the implantation zone in which the medical intervention means is to be implanted; introducing around the guide wire an elongated mandrel disposed within an elongated sheath; withdrawing the guide wire and the mandrel from the patient's body; providing the catheter with an inner strengthening cable adapted to be removably disposed within the catheter; introducing, into the sheath extending to the implantation zone, the medical intervention means first and then the catheter; withdrawing the sheath from the patient's body while leaving the medical intervention means in the implantation zone; withdrawing the strengthening cable from the catheter; and cutting the catheter at the proximal end, near the skin surface;

providing a locating member on the proximal end of the stem, the locating member being adapted to being disposed subcutaneously for locating the stem through the skin surface of the body;

disposing the locating member and the proximal end of the stem subcutaneously in the body in proximity to the access route, the step of disposing including forming, within the patient's body in proximity to the access route, a small space for disposing therein the locating member fixed to the proximal end; and closing the access route, whereby the locating member, the stem, and the medical intervention means remain disposed in the body.

7. A method for medically operating within a patient's body by means of an implantable apparatus comprising a medical intervention means adapted for medically operating within an implantation zone of the body and a divisible extension stem implantable within the body, the stem having a proximal and a distal end, and said medical interventions means being fixed to the distal end, the method comprising the steps of:

forming an access route to a blood vessel through a skin surface of the body, said step of forming an access route including one of forming said access route percutaneously and forming said access route by denudation of said blood vessel;

introducing the apparatus into the body through the access route with the medical intervention means first so as to implant said intervention means in the implantation zone, the stem having a length sufficient to extend along the route;

wherein the length of the stem is such that the proximal end thereof extends out of the patient's body when the medical intervention means is introduced into the implantation zone, the method comprising the further step of cutting the stem at the proximal end before providing the proximal end with the locating member, whereby the length of the stem is adapted to the length of the access route;

providing a locating member on the proximal end of the stem, the locating member being adapted to being disposed subcutaneously for locating the stem through the skin surface of the body;

disposing the locating member and the proximal end of the stem subcutaneously in the body in proximity to the access route; and closing the access route, whereby the locating member, the stem, and the medical intervention means remain subcutaneously disposed in the body.

8. A method for medically operating within a patient's body by means of an implantable apparatus comprising a medical intervention means adapted for medically operating within an implantation zone of the body and a divisible extension stem implantable within the body, the stem having a proximal and a distal end, and said medical interventions means being fixed to the distal end, the method comprising the steps of:

forming an access route to an implantation zone through a skin surface of the body;

introducing the apparatus into the body through the access route with the medical intervention means first so as to implant said intervention means in the implantation zone, the stem having a length sufficient to extend along the route;

wherein the length of the stem is such that the proximal end thereof extends out of the patient's body when the medical intervention means is introduced into the implantation zone, the method comprising the further step of cutting the stem at the proximal end before providing the proximal end with the locating member, whereby the length of the stem is adapted to the length of the access route;

providing a locating member on the proximal end of the stem, the locating member being adapted to being disposed subcutaneously for locating the stem through the skin surface of the body;

disposing the locating member and the proximal end of the stem subcutaneously in the body in proximity to the access route, said step of disposing including forming, within said patient's body in proximity to said access route and close to said skin surface, a small space for disposing therein said locating member fixed to said proximal end, whereby said locating member is detectable by palpation though said skin surface; and closing the access route, whereby the locating member, the stem, and the medical intervention means remain subcutaneously disposed in the body.

* * * * *